(12) United States Patent
Xu et al.

(10) Patent No.: US 11,780,905 B2
(45) Date of Patent: Oct. 10, 2023

(54) PREPARATION METHOD FOR COLLAGEN HYDROGEL

(71) Applicant: Jiangnan University, Wuxi (CN)

(72) Inventors: Fei Xu, Wuxi (CN); Jinyuan Hu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 137 days.

(21) Appl. No.: 17/169,631

(22) Filed: Feb. 8, 2021

(65) Prior Publication Data

US 2021/0163576 A1   Jun. 3, 2021
US 2023/0257445 A9   Aug. 17, 2023

(30) Foreign Application Priority Data

Jun. 29, 2020   (CN) .......................... 202010610348.8

(51) Int. Cl.
    *C07K 14/195*   (2006.01)
    *C07K 14/78*    (2006.01)
    *C12N 1/20*     (2006.01)
    *C12N 15/70*    (2006.01)
    *C12R 1/19*     (2006.01)

(52) U.S. Cl.
    CPC .............. *C07K 14/78* (2013.01); *C12N 1/20* (2013.01); *C12N 1/205* (2021.05); *C12N 15/70* (2013.01); *C12R 2001/19* (2021.05)

(58) Field of Classification Search
    CPC .......... A61K 8/65; C12N 15/70; C07K 14/78; C07K 2319/21
    USPC ....... 514/17.2; 435/320.1, 252.23, 69.1, 69.7
    See application file for complete search history.

(56) References Cited

PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*

* cited by examiner

*Primary Examiner* — Robert B Mondesi
*Assistant Examiner* — Mohammad Y Meah
(74) *Attorney, Agent, or Firm* — IPRO, PLLC; Na Xu

(57) ABSTRACT

The disclosure provides an active peptide with an anti-lipid oxidation function and a preparation method and application thereof and belongs to the technical field of plant-derived biologically active peptides. In the disclosure, oil processing by-products, namely oil crops after oil extraction, are used as the raw materials, and the raw materials are subjected to the steps of protein extraction, infrared pretreatment, proteolysis, freeze-drying, lipophilic part extraction, vacuum concentration and drying to prepare an anti-lipid oxidation peptide having the functional characteristics of scavenging DPPH free radicals, chelating metal ions, inhibiting lipid peroxidation, prolonging vegetable oil oxidation induction time, improving emulsion stability and the like. The anti-lipid oxidation peptide can be used as a natural antioxidant in the storage and preservation of lipid and other lipid-containing food, the problems of product deterioration and harmful product production caused by lipid oxidation are solved, and the shelf life of food is prolonged.

6 Claims, 9 Drawing Sheets

Specification includes a Sequence Listing.

PREPARATION METHOD FOR COLLAGEN HYDROGEL

REFERENCE TO SEQUENCE LISTING

The instant application contains a Sequence Listing in TXT format as a file named "seq.txt", created on Oct. 14, 2022, of 27 KB in size, and which is hereby incorporated by reference in its entirety.

TECHNICAL FIELD

The disclosure herein relates to a preparation method for collagen hydrogel, and belongs to the technical field of gene engineering.

BACKGROUND

Collagen, a triple helix formed by intertwining three chains, is the most abundant protein in mammals and accounts for ⅓ of human proteins, and can be highly specifically assembled to form collagen fibers, and as the main component of an extracellular matrix, it can control the growth and differentiation of cells, and can be used for repairing and regenerating human tissues and organs. Collagen hydrogel is a biodegradable water-rich three-dimensional material that can provide biological signals and serve as a cell scaffold to provide a microenvironment required for cell growth, differentiation and migration, and can be used as an articular cartilage filler.

Currently, there are mainly five sources of collagen as follows. At present, the most important source is animal skin extraction, the price is low, but it tends to carry disease sources. Chemically synthesized polypeptide has high controllability and purity, the most obvious disadvantages are that the price is high, the length is limited, and it is not suitable for batch production. Expression via eukaryotic systems such as transgenic plants and mammalian cells has the advantages that correct folding of proteins can be guided and complex post-translational processing functions are provided, but the common problems are high culture cost, long period, low expression amount and difficulty in large-scale production. A microbial expression system has obvious advantages of low cost, high expression amount and the appearance. Recent studies have shown that more and more mammal and bacterial collagen has been proved to be efficiently and heterologously expressed in hosts such as bacteria and yeast, and correctly folded into collagen triple helices. Recombinant collagen has potential applications in the production of biomaterials, but it lacks the driving force of self-assembly to form higher structures and fails to form a higher structure, which limits its applications in biomaterials and tissue engineering. Barbara Brodsky and Magnus Hook et al. have demonstrated that modified collagen can serve as a substrate for fibroblasts, endothelial cells and smooth muscle cells by heterologous expression of collagen Scl2 with integrin action sites inserted in *Streptococcus pyogenes* in *E. coli*[1,2]. Molly M. Stevens et al. have studied that by inserting hyaluronic acid and chondroitin sulfate binding sites in an Scl2 sequence, followed by cross-linking using metal matrix hydrolase 7 (MMP7) sensitive peptides, biodegradable hydrogel is formed, which is expected to be useful in the regeneration of articular cartilage[3].

1. An, B., et al., *The influence of specific binding of collagen-silk chimeras to silk biomaterials on hMSC behavior*. Biomaterials, 2013. 34(2): p. 402-412.
2. Seo, N., et al., *An engineered α1 integrin-binding collagenous sequence*. Journal of Biological Chemistry, 2010. 285(40): p. 31046-31054.
3. Cosgriff-Hernandez, E., et al., *Bioactive hydrogels based on Designer Collagens*. Acta Biomaterialia, 2010. 6(10): p. 3969-3977.

SUMMARY

According to the present disclosure, high-aggregation self-assembly of collagen is promoted to form collagen hydrogel by fusing and expressing E3 and K3 heterologous α-helices at an N end and a C end of the collagen.

The present disclosure provides a collagen molecule, and a peptide chain forming the collagen molecule has the following structure:
  (a) an E3 α helix, a V-domain, a plurality of repeated GXYs and a K3 α helix contained in sequence; and
  (b) a protein derived from (a) by deleting, substituting, increasing or decreasing one or more amino acids of CL-domain on the basis of (a), and having functional properties of (a).

In one implementation, the peptide chain forming the collagen molecule has the following structure:
  (a)

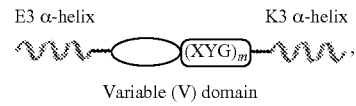

Variable (V) domain where an amino acid sequence includes: an E3 α helical structure, a V-domain, a collagen region with repeated amino acid units (GXYs), and a K3 α helical structure in sequence; an amino acid sequence of the V-domain is set forth as SEQ ID NO:1; an amino acid sequence of the E3 α helical structure is EISALEKEISALEKEISALEK (SEQ ID NO:15); an amino acid sequence of the K3 α helical structure is KISALKEKISALKEKISALKE (SEQ ID NO:16); the $(GXY)_m$ is the collagen region, and m is an integer $\geq 2$; and an amino acid sequence of the $(GXY)_m$ includes, but is not limited to, the sequence set forth as SEQ ID NO:4, or a repeated sequence including a plurality of sequences set forth as SEQ ID NO:4; and
  (b) a protein derived from (a) by deleting, substituting, increasing or decreasing one or more amino acids of the collagen region on the basis of (a), and having functional properties of (a).

In one implementation, 6×His tags are further fused in front of the E3 α helix.

In one implementation, the E3 α helix and the K3 α helix are respectively fused and linked with the collagen region through flexible linker peptide; and the flexible linker peptide includes, but is not limited to, glycine.

The present disclosure further provides collagen hydrogel formed by self-assembly of trimeric collagen molecules.

The present disclosure further provides a gene encoding the collagen molecule or encoding a peptide chain of the collagen molecule.

In one implementation, the gene includes a nucleotide sequence set forth as any one of SEQ ID NOS:9-12.

The present disclosure further provides a plasmid or cell carrying a gene.

In one implementation, the plasmid includes, but is not limited to: pColdIII plasmids and pET plasmids.

In one implementation, the plasmid is pColdIII.

In one implementation, the cell is an E. coli cell, including, but not limited to, E. coli BL21, E. coli BL21(DE3), E. coli JM109, E. coli DH5α, or E. coli TOP10.

The present disclosure further provides a preparation method for type I collagen hydrogel, and the method includes the following steps:

(1) synthesizing a gene encoding a chimeric α-helical collagen peptide chain;
(2) linking the gene synthesized in step (1) with a vector, and transforming the gene into a target cell for expression and purification; and
(3) dialyzing a collagen solution obtained in step (2) at 0~4° C.

In one implementation, the preparation method includes the following steps:

(1) constructing collagen recombinant plasmids: synthesizing genes VB, $E_3$-VB-$K_3$, $E_3$-VBB-$K_3$ and $E_3$-VBBB-$K_3$ encoding collagen set forth as SEQ ID NOS:9-12 respectively, and constructing the genes on plasmids pColdIII-Tu respectively, where the pColdIII-Tu is obtained by mutating plasmids pColdIII to introduce an Nco I site by taking pCOLD-TU(Nco I)-S: CTCGAGGGATCCGAATTCA (set forth as SEQ ID NO:13) and pCOLD-TU(Nco I)-A: GAGCTC-CATGGGCACTTTG (set forth as SEQ ID NO:14) as primers;
(2) transforming: transforming the recombinant plasmids into E. coli BL21(DE3) respectively;
(3) inducing expression: culturing a single colony in an LB liquid culture medium overnight, then transferring into a TB liquid culture medium at an inoculation amount of 1%, culturing for 24 h at 37° C., adding IPTG, inducing for 10 h at 25° C., and inducing for 14 h at 15° C.;
(4) purifying: collecting fermented bacteria, resuspending the bacteria by using a phosphate buffer solution, crushing cells by using an ultrasonic cell crusher under an ice bath condition, centrifuging at 10,000 rpm for 20 min at 4° C. to remove cell fragments, and filtering a supernatant by using a microporous filter membrane to remove impurities; injecting a sample into a His-trap hp affinity chromatography column (5 mL) mounted on a protein purifier, then flushing by eight column volumes with a washing solution, increasing imidazole content in an elution buffer solution stepwise (140 mM, 164 mM and 400 mM) to elute proteins, and collecting appearance proteins at a 400 mM imidazole concentration; and
(5) dialyzing a collagen solution obtained in step (4) by using ultrapure water or a 10 mM phosphate buffer solution at 4° C.

In one implementation, the dialysis is to dialyze collagen with a molecular weight cut-off greater than or equal to 7 kDa.

The present disclosure further provides application of collagen in preparation of hydrogel.

In one implementation, the application is to condition the collagen for dialysis in water or a phosphate buffer solution such that after a concentration is greater than or equal to 10 mg/mL, the hydrogel is formed after standing for 3 days at 4° C.

The present disclosure further provides a method for controlling a swelling property or a mechanical property of hydrogel. The method is configured to control the number of amino acids of $(GXY)_m$ in collagen molecules expressed by microbial cells, where m is 27, 54 and 81, corresponding to a region B in Streptococcus pyogenes collagen Scl1, double-length B and triple-length B respectively, and then the hydrogel is prepared from the collagen molecules produced by microbial fermentation.

The collagen, the gene, the plasmid, the cell or the preparation method provided by the present disclosure can be applied to the fields of biology, chemical industry, food, medicine, biological materials, tissue engineering, cosmetics and the like.

Beneficial effects: 1. On the basis of N-end and C-end heterologous α helix E3 and K3 sequences, a continuous Gly-Xaa-Yaa triplet collagen sequence is inserted therebetween to form a three-segment chimeric collagen E3 α-helix-V-collagen-K3 α-helix with α helices at the N end and the C end respectively. Self-assembly is driven by interaction of E3 and K3 heterologous α helices at the N end and the C end to form the collagen hydrogel.

2. According to the present disclosure, the collagen sequence involved in the present disclosure is expressed by E. coli cold shock to prepare the collagen hydrogel which can be self-assembled from a clean source, the preparation process is simple, and the collagen hydrogel can be produced on a large scale at low cost. The preparation method and a sequence design mode thereof are provided for preparing the collagen hydrogel, a collagen region of the sequence can be replaced and expanded, a platform is provided for research and application based on the collagen hydrogel, and the collagen hydrogel has a wide prospect in biomaterial application.

3. The present disclosure also regulates a gel property and water content of the hydrogel by adjusting a sequence length of the collagen region. The mechanical property and water content of the collagen hydrogel can be controlled by controlling the collagen region to be of 27, 54 and 81 Gly-Xaa-Yaa triplets.

DETAILED DESCRIPTION

Materials and methods used in the present disclosure are as follows.

1) Culture Media:

LB solid culture medium: 15 g/L agar, 10 g/L tryptone, 5 g/L yeast extract powder, and 10 g/L NaCl, where pH is 7.0.

LB liquid culture medium: 10 g/L tryptone, 5 g/L yeast extract powder, 10 g/L of NaCl, where pH is 7.0.

TB liquid culture medium: 12 g/L tryptone, 24 g yeast extract powder, 4 mL glycerol, 2.31 g $KH_2PO_4$, and 12.54 g $K_2HPO_4$, where pH is 7.5, and a volume is set to 1 L.

2) A Bacteria Culture Method:

*E. coli* seed culture conditions: single colonies grown by plate streaking are inoculated into the LB liquid culture medium, a liquid loading amount is 10%, a 250 mL shake flask is adopted for culture, a culture temperature is 37° C., a culture time is 10 h, and a rotation speed is 200 rpm.

Fermentation culture conditions of a pET28a recombinant strain: the TB culture medium is adopted, a liquid loading amount of the culture medium is 20%, an inoculation amount is 1%, a 500 mL shake flask is adopted for culture, a culture temperature is 25° C., when $OD_{600}$ reaches 2.5 h, IPTG with a final concentration of 1 mM is adopted for induction, an induction temperature is 35° C., an induction time is 24 h, and a rotation speed is 200 rpm.

Fermentation culture conditions of a pCold recombinant strain: the TB culture medium is adopted, a liquid loading amount of the culture medium is 20%, an inoculation amount is 1%, a 500 mL shake flask is adopted for culture, IPTG with a final concentration of 1 mM is adopted for induction after the strain is cultured for 24 h at 37° C., induction is performed for 10 h at 25° C. and then performed for 14 h at 15° C., and a rotation speed is 200 rpm.

Embodiment 1 Sequence Design and Sample Preparation

Designing is performed according to a structure shown by E3-V-$(GXY)_m$-K3, where E3 α-helix represents EISALEKEISALEKEISALEK (SEQ ID NO:15), V-domain represents a globular domain guiding the correct folding of a collagen region, $(GXY)_m$ represents the collagen region capable of being designed and changed, and K3 α-helix represents KISALKEKISALKEKISALKE (SEQ ID NO:16); and the specific steps are as follows.

Figure 1A:
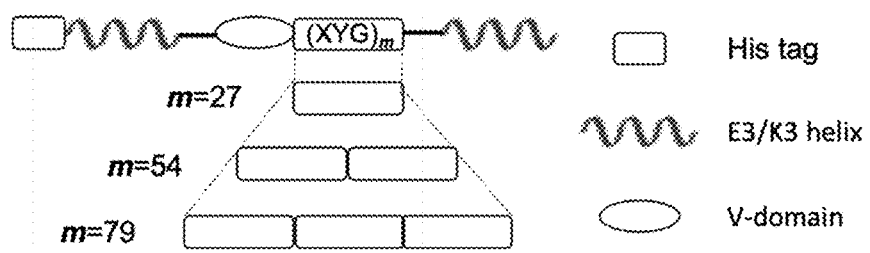
FIG. 1A is a pattern diagram of a three-segment chimeric sequence E3-collagen-K3, the lengths of collagen regions of the three sequences being of 27, 54 and 79 GXY triplets respectively which correspond to single-length, double-length and triple-length collagen Scl2-B sequences.
Figure 1B:
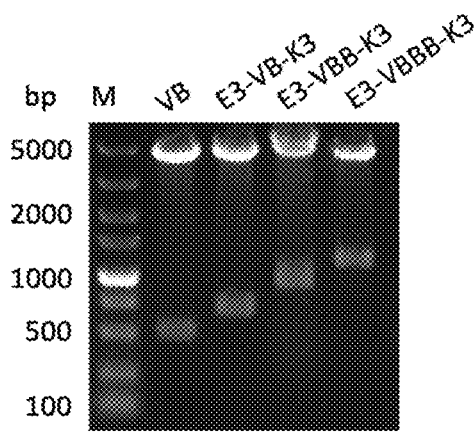
FIG. 1B is a double-enzyme digestion verification diagram of a recombinant plasmid.

(1) The E3 α-helix at an N end and the K3 α-helix at a C end are used as fixed sequence motifs, and the variable collagen region and the globular V-domain guiding the correct folding of the collagen region are inserted between the E3 α-helix and the K3 α-helix at the C end to obtain a three-segment chimeric sequence, abbreviated as E3-Vcollagen-K3 as shown in FIG. 1A. Collagen Scl2 (Genbank ID: AAL50184.1) from *Streptococcus pyogenes* is used as bacterial collagen in a collagen regional sequence in the present embodiment, and an Scl2 collagen region is divided into three equal-length regions A, B and C. In the present embodiment, designed CL domains are B, BB (two repeated B regions) and BBB (three repeated B regions) respectively.

(2) The globular V-domain (set forth as SEQ ID NO:1) derived from Scl2 is inserted at the N end of the collagen sequence and used for guiding the correct folding of a collagen triple helix, an integrin binding site is inserted between the collagen sequences for realizing a biological function, and 6×His is inserted at the N end of the entire sequence for purification.

An amino acid sequence is designed as follows:

```
VB (containing 6xHis tags):
                                      (SEQ ID NO: 17)
HHHHHHADEQEEKAKVRTELIQELAQGLGGIEKKNFPTLGDEDLDHTYMT

KLLTYLQEREQAENSWRKRLLKGIQDHALDPGPRGEQGPQGLPGKDGEAG

AQGPAGPMGPAGFPGERGEKGEPGTQGAKGDRGETGPVGPRGERGEAGPA

GKDGERGPVGPAG;

E3-VB-K3 (containing 6xHis tags):
                                      (SEQ ID NO: 18)
HHHHHHGEISALEKEISALEKEISALEKGGGGGGGADEQEEKAKVRTELI

QELAQGLGGIEKKNFPTLGDEDLDHTYMTKLLTYLQEREQAENSWRKRLL

KGIQDHALDPGPRGEQGPQGLPGKDGEAGAQGPAGPMGPAGFPGERGEKG

EPGTQGAKGDRGETGPVGPRGERGEAGPAGKDGERGPVGPAGGGGGGGGK

ISALKEKISALKEKISALKE;

E3-VBB-K3 (containing 6xHis tags):
                                      (SEQ ID NO: 19)
HHHHHHGEISALEKEISALEKEISALEKGGGGGGGADEQEEKAKVRTELI

QELAQGLGGIEKKNFPTLGDEDLDHTYMTKLLTYLQEREQAENSWRKRLL

KGIQDHALDPGPRGEQGPQGLPGKDGEAGAQGPAGPMGPAGFPGERGEKG

EPGTQGAKGDRGETGPVGPRGERGEAGPAGKDGERGPVGPAGPRGEQGPQ

GLPGKDGEAGAQGPAGPMGPAGFPGERGEKGEPGTQGAKGDRGETGPVGP

RGERGEAGPAGKDGERGPVGPAGGGGGGGGKISALKEKISALKEKISALK

E;

E3-VBBB-K3 (containing 6xHis tags):
                                      (SEQ ID NO: 20)
HHHHHHGEISALEKEISALEKEISALEKGGGGGGGADEQEEKAKVRTELI

QELAQGLGGIEKKNFPTLGDEDLDHTYMTKLLTYLQEREQAENSWRKRLL

KGIQDHALDPGPRGEQGPQGLPGKDGEAGAQGPAGPMGPAGFPGERGEKG

EPGTQGAKGDRGETGPVGPRGERGEAGPAGKDGERGPVGPAGPRGEQGPQ
```

-continued

```
GLPGKDGEAGAQGPAGPMGPAGFPGERGEKGEPGTQGAKGDRGETGPVGP

RGERGEAGPAGKDGERGPVGPAGPRGEQGPQGLPGKDGEAGAQGPAGPMG

PAGFPGERGEKGEPGTQGAKGDRGETGPVGPRGERGEAGPAGKDGERGPV

GPAGGGGGGGGKISALKEKISALKEKISALKE;
```

Genes encoding the above amino acid sequence are synthesized. A nucleotide sequence encoding VB is set forth as SEQ ID NO:9; a gene sequence encoding E3-VB-K3 is set forth as SEQ ID NO:10; a gene sequence encoding E3-VBB-K3 is set forth as SEQ ID NO:11; a gene sequence encoding E3-VBBB-K3 is set forth as SEQ ID NO:12; and the nucleotide sequences shown above each contain a 5' Nco I digestion site, a 5' flanking sequence GC, and a 3' Bam HI digestion site respectively. The synthesized genes are respectively inserted between NcoI and BamHI of pCOLD III-Tu plasmids to obtain corresponding recombinant collagen plasmids, then the recombinant plasmids are respectively transformed into $E.\ coli$ BL21(DE3) competent cells by a $CaCl_2$ method, an LB plate containing antibiotics is coated, culturing and screening are performed, and a recombinant strain for preparing hybrid collagen is obtained; and the plasmids pCOLD III-Tu are obtained by mutating plasmids pColdIII to introduce the Nco I site by taking pCOLD-TU(Nco I)-S: CTCGAGGGATCCGAATTCA (set forth as SEQ ID NO:13) and pCOLD-TU(Nco I)-A: GAGCTC-CATGGGCACTTTG (set forth as SEQ ID NO:14) as primers.

Figure 1C:
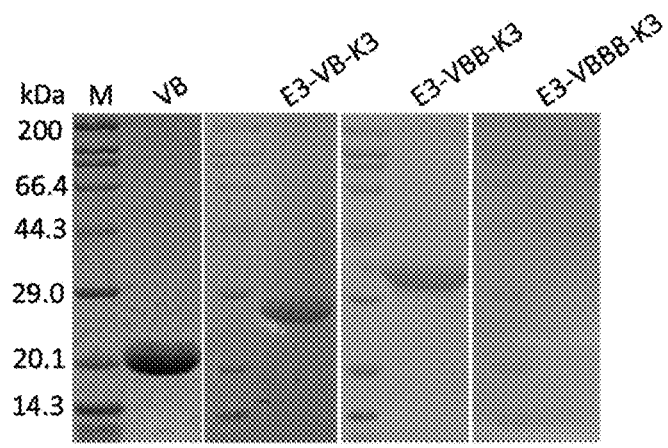
FIG. 1C is purified collagen SDS-PAGE.
Figure 2A:
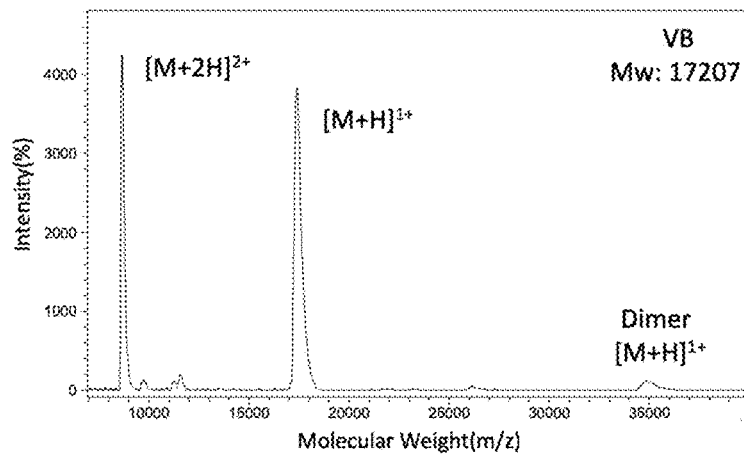
FIG. 2A is MALDI-TOF molecular weight identification of designed collagen VB.
Figure 2B:
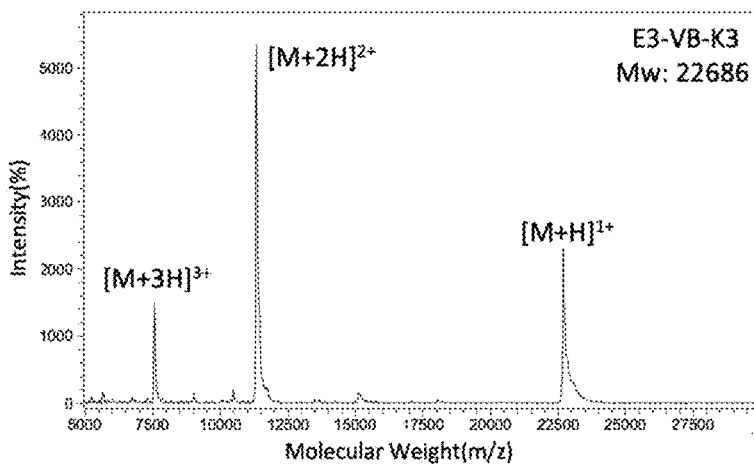
FIG. 2B is MALDI-TOF molecular weight identification of designed collagen E3-VB-K3.
Figure 2C:
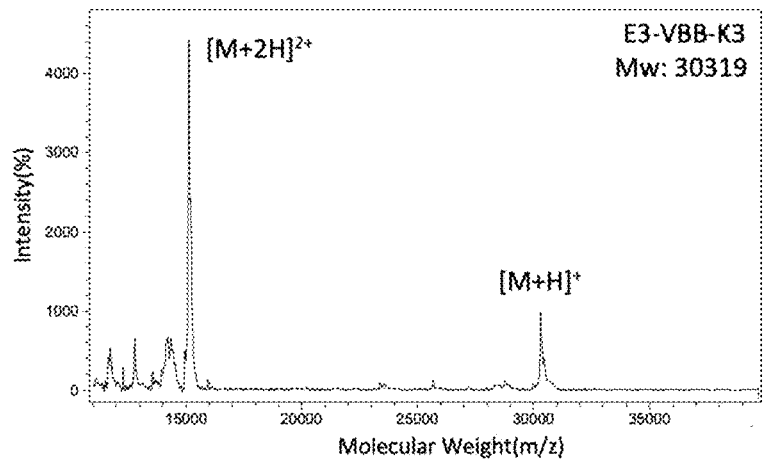
FIG. 2C is MALDI-TOF molecular weight identification of designed collagen E3-VBB-K3.
Figure 2D:
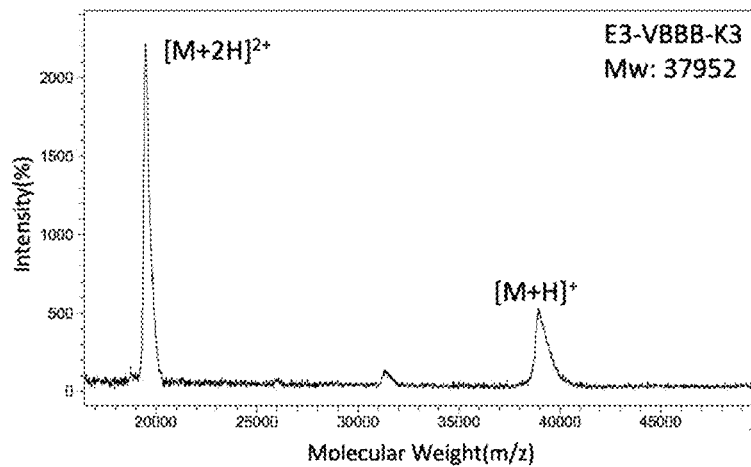
FIG. 2D is MALDI-TOF molecular weight identification of designed collagen E3-VBBB-K3.

After recombinant strains are respectively induced to be fermented, a fermentation broth is centrifuged at 8,000 rpm for 5 min, and fermented bacteria are collected. The bacteria are resuspended in a phosphate buffer solution, cells are crushed by an ultrasonic cell crusher under an ice bath condition and centrifuged at 10,000 rpm for 20 min at 4° C. to remove cell fragments, and a supernatant is filtered through a microporous filter membrane (0.45 µm) to remove impurities. A sample is injected into a 5 mL His-trap hp affinity chromatography column mounted on a protein purifier, then 8 column volumes are flushed with a washing solution, imidazole content in an elution buffer solution is increased stepwise (140 mM and 400 mM) to elute proteins, and appearance proteins are collected and subjected to SDS-PAGE electrophoresis analysis. Desalting is then performed through a desalting column, freeze drying is performed, a small amount of lyophilized powder is taken and dissolved in water, and SDS-PAGE and Maldi-tof are adopted for identification. FIG. 1C shows that single bands are detected in all the purified proteins by SDS-PAGE, and since collagen is a rod-like protein and a protein Marker is a globular molecule, a molecular weight shown by SDS-PAGE is larger than an expected molecular weight position. As shown in FIGS. 2(A)-(D), a molecular weight obtained by mass spectrometry is consistent with a theoretical molecular weight, and collagen with a correct molecular weight is obtained.

Embodiment 2 Secondary Structure Determination of Collagen

The collagen prepared in Embodiment 1 is formulated to a concentration of 1 mg/mL respectively. Then the collagen is subjected to standing for 24 h or more at 4° C., and circular dichroism spectrum full-wavelength scanning is performed in a 1 mm cuvette at 4° C. with a wavelength from 190 nm to 260 nm, and a wavelength interval of 1 nm, and the scanning remains for 5 s at each wavelength. A thermal change experiment measures at 220 nm at a temperature ranging from 4° C. to 80° C., equilibration is performed at each temperature for 8 s, and a temperature increasing rate is 1° C./6 min. A typical collagen triple helix CD spectrum shows a positive absorption peak at 220 nm, a variable globular domain used for guiding folding is rich in α-helix, and there are characteristic negative absorption peaks at 208 nm and 222 nm.

Figure 3A:
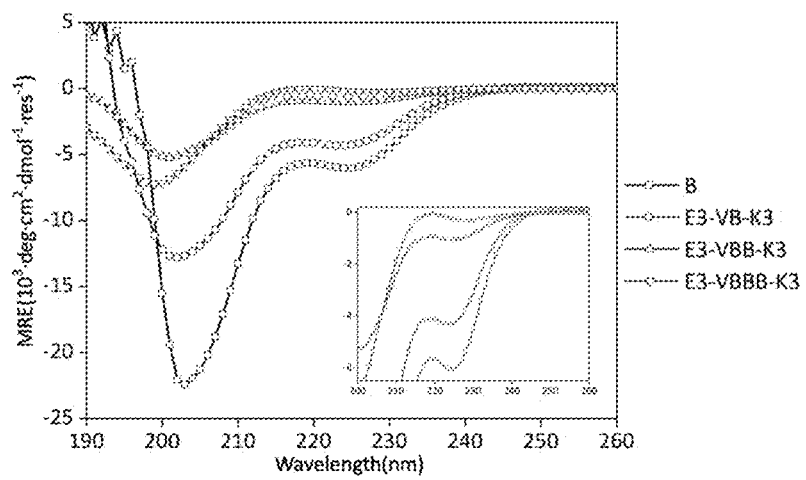
FIG. 3A is circular dichroism spectrum full-wavelength scanning spectrum of designed collagen.
Figure 3B:
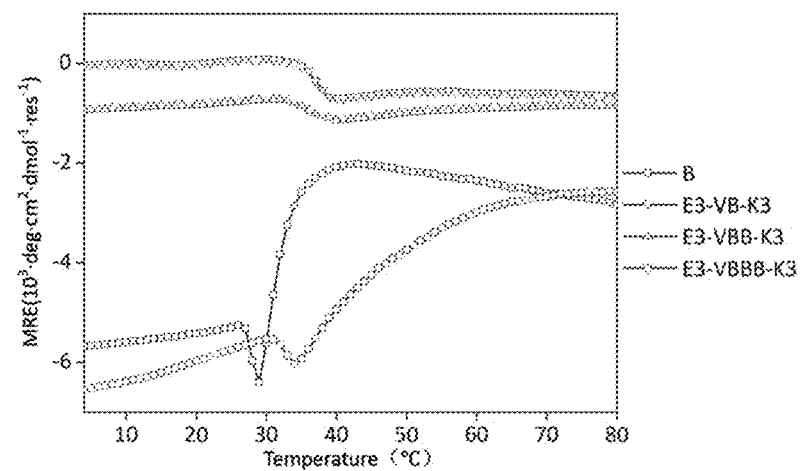
FIG. 3B is a circular dichroism spectrum thermal change curve of designed collagen.
Figure 4A:
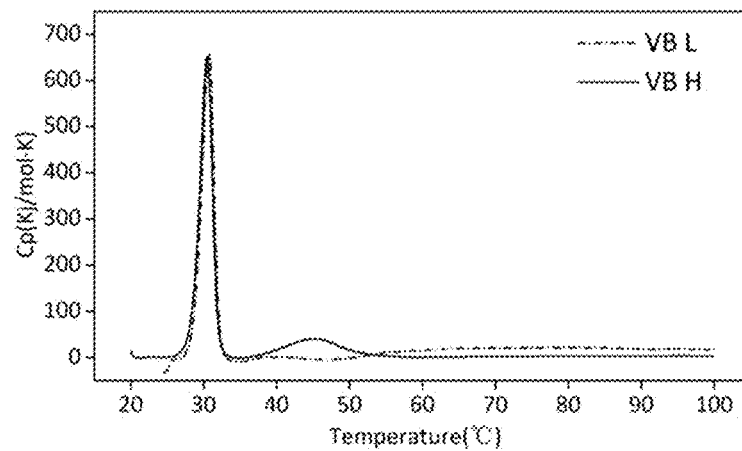
FIG. 4A is differential scanning calorimetry (DSC) measurement of designed collagen VB at low (L) and high (H) concentrations.
Figure 4B:
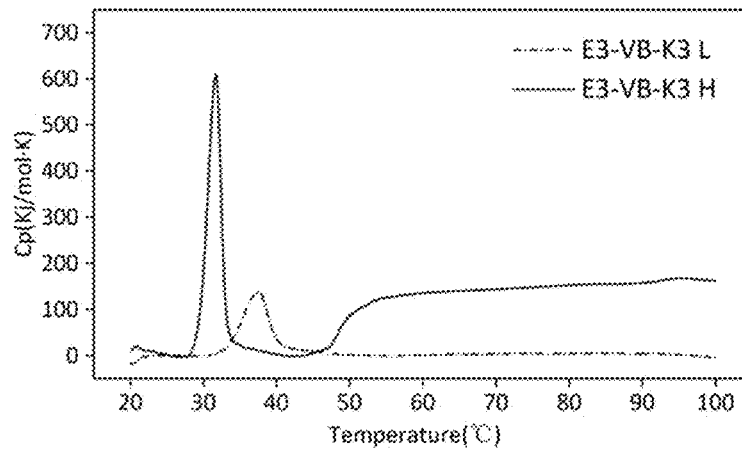
FIG. 4B is differential scanning calorimetry (DSC) measurement of designed collagen E3-VB-K3 at low (L) and high (H) concentrations.
Figure 4C:
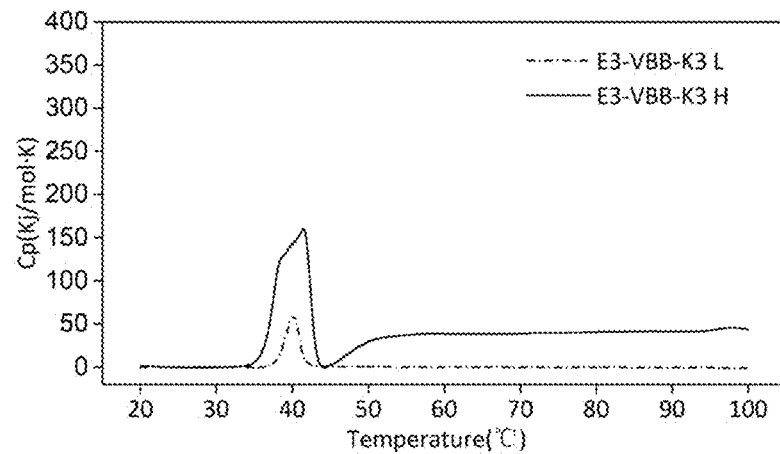
FIG. 4C is differential scanning calorimetry (DSC) measurement of designed collagen E3-VBB-K3 at low (L) and high (H) concentrations.
Figure 4D:
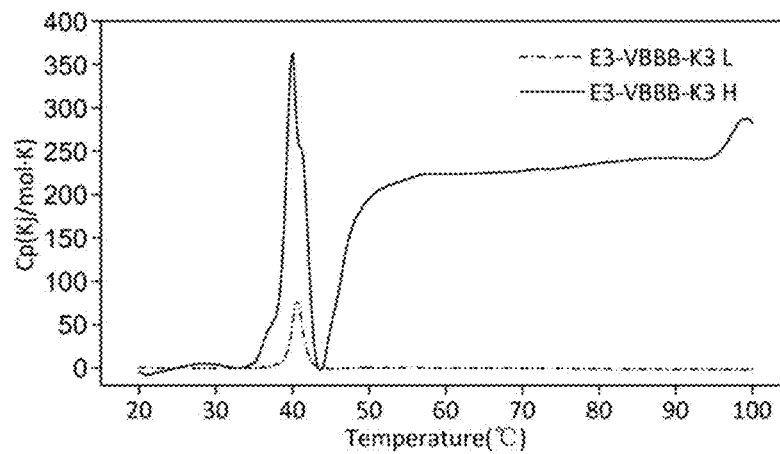
FIG. 4D is differential scanning calorimetry (DSC) measurement of designed collagen E3-VBBB-K3 at low (L) and high (H) concentrations.
Figure 5A:
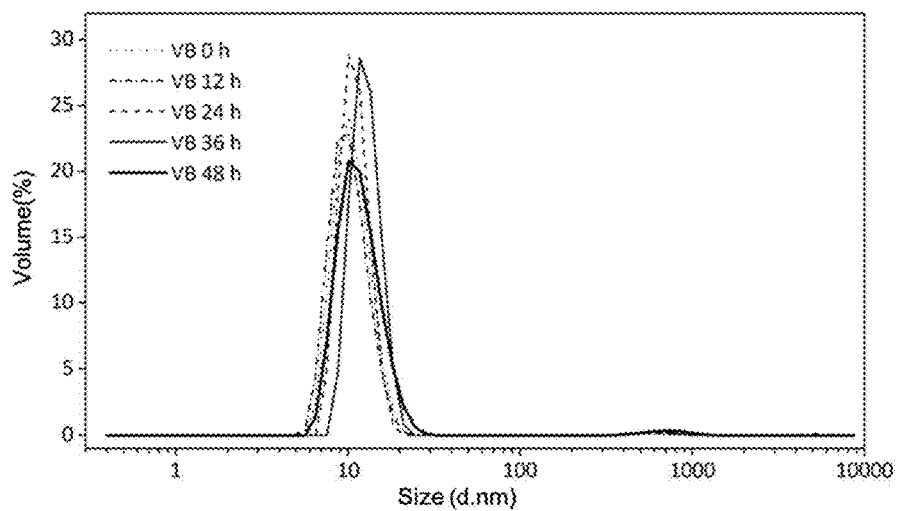
FIG. 5A is a hydration particle size of VB self-assembled polymer at different times as determined by dynamic light scattering.
Figure 5B:
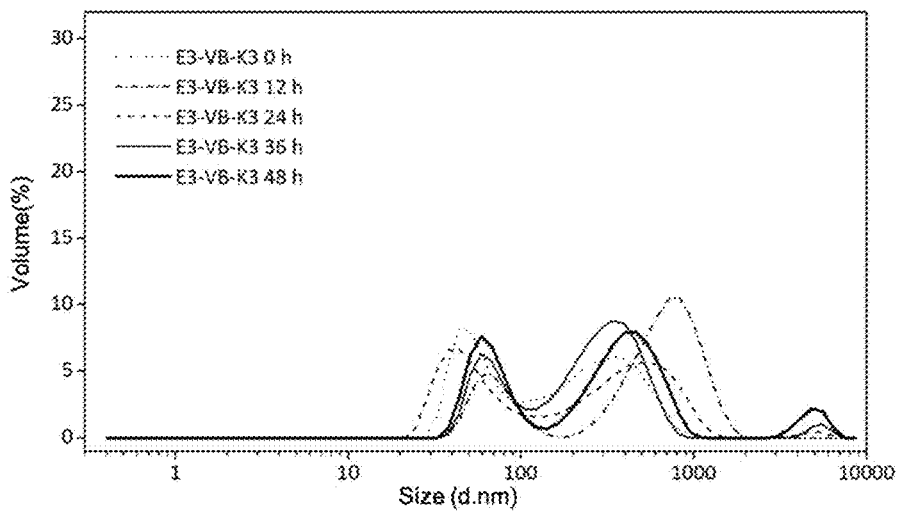
FIG. 5B is a hydration particle size of E3-VB-K3 self-assembled polymer at different times as determined by dynamic light scattering.
Figure 5C:
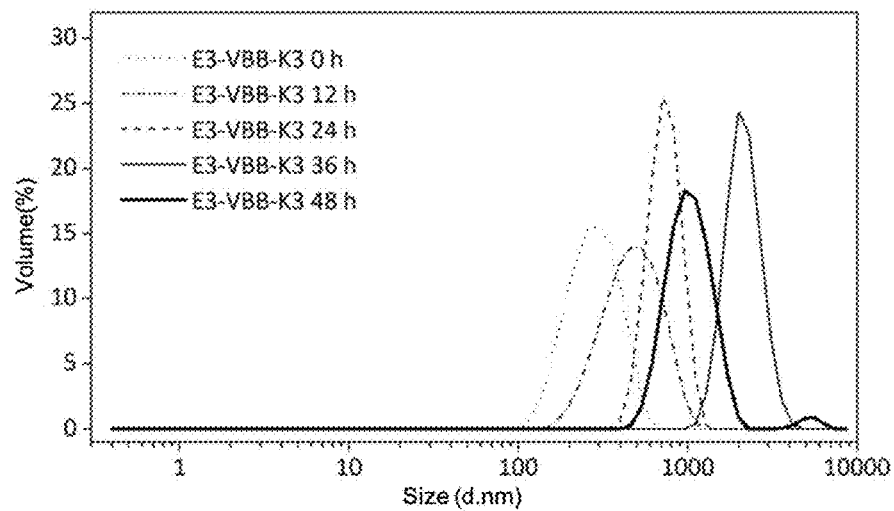
FIG. 5C is a hydration particle size of E3-VBB-K3 self-assembled polymer at different times as determined by dynamic light scattering.
Figure 5D:
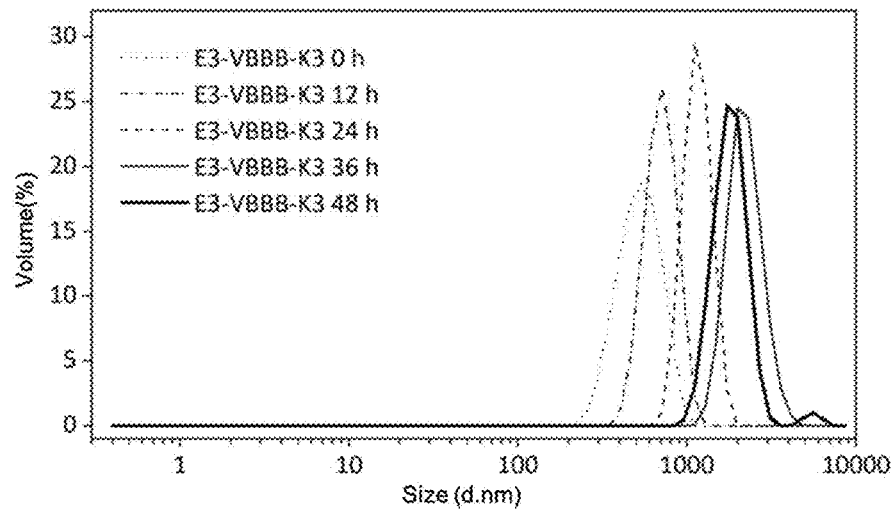
FIG. 5D is a hydration particle size of E3-VBBB-K3 self-assembled polymer at different times as determined by dynamic light scattering.

As shown in FIG. 3A and FIG. 3B, under full-wavelength scanning, the designed protein of Embodiment 1 shows superposition absorption signals of the α-helices and a collagen triple helix, and has the characteristic absorption peaks around 220 nm; the results of the thermal change experiment show that with the increase of temperature, a characteristic absorption value at 220 nm is changed sharply at 30-40° C., which is manifested as destroyed secondary structure of the collagen. That is, the triple helix is uncoiled. The results of the CD full spectrum and the thermal change experiment show that the three-segment chimeric collagen designed in Embodiment 1 can be correctly folded to form a collagen triple helix structure, and has high thermal stability.

Embodiment 3 Detection of Intermolecular Interaction by a Differential Scanning Calorimetry Collagen E3-VB-K3, E3-VBB-K3 and E3-VBBB-K3 purifying solutions prepared in Embodiment 1 are dialyzed by 10 mM PB in a dialysis bag with a molecular weight cut-off of 7 kDa. In the process of dialysis, collagen molecules are continuously aggregated to form a precipitate, the precipitate is collected and prepared into a 10 mg/mL solution, VB cannot be aggregated to form a precipitate in the process of dialysis, and the VB prepared by freeze drying is prepared into a solution with the same concentration. A concentration of a sample with a low concentration is 1.5 mg/mL. Then the sample stands for 24 h or more at 4° C., a thermal change temperature is measured by a differential scanning calorimetry, a temperature scan range is 0-100° C., and a temperature increasing rate is 1° C./min. As shown in FIG. 4A~4D, only a thermal change temperature of a triple helix of the VB is detected as 30.34° C. at the low concentration, and similar to the CD results. At a high concentration, a thermal change peak of 45.16° C. is also detected and is a thermal change temperature of a globular domain, which proves that a collagen region and a guided folding domain are both correctly folded and the structure is stable. Only thermal change temperatures of triple helix regions are detected in E3-VB-K3, E3-VBB-K3 and E3-VBBB-K3 at the low concentration, which proves that collagen regions are folded correctly to form stable triple helices. At the high concentration, in addition to the thermal change temperature at which the triple helix is uncoiled, a gradual transition temperature can be detected, which may be due to the heterogeneity of molecule interaction of E3 and K3.

Embodiment 4 Self-Assembly of Collagen

Collagen VB, E3-VB-K3, E3-VBB-K3 and E3-VBBB-K3 solutions are prepared according to the method of Embodiment 1, a buffer solution is replaced with 10 mM PB by using a HiTrap desalting column, the solution stands in a 4° C. refrigerator and is sampled every 12 h for measuring a hydration particle size thereof by dynamic light scattering. The process of self-assembly is observed, and the results show that, as in FIG. 5A~5D, a VB particle size does not change along with time, and particle sizes of E3-VB-K3, E3-VBB-K3 and E3-VBBB-K3 are gradually increased along with the time, which indicates that small molecules of collagen are continuously self-assembled and aggregated into large particles along with the time, where the particle size of the E3-VB-K3 after being self-assembled for 24-48 h can reach 4,883 nm; and the results of the aggregation process also show that a proportion of large particles becomes larger along with the time. The particle size of the E3-VBB-K3 after being self-assembled for 24-48 h can reach 5,560 nm; and the particle size of the E3-VBBB-K3 after being self-assembled for 24-48 h can reach 5,560 nm.

Embodiment 5 Internal Structure and Mechanical Property of Hydrogel

Figure 6A:
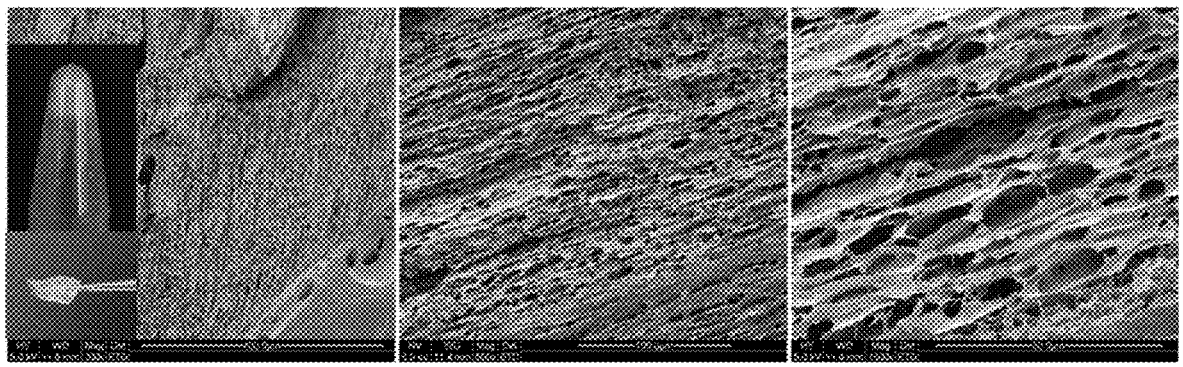
FIG. 6A is a scanning electron micrograph of collagen hydrogel and a hydrogel image for E3-VB-K3.
Figure 6B:
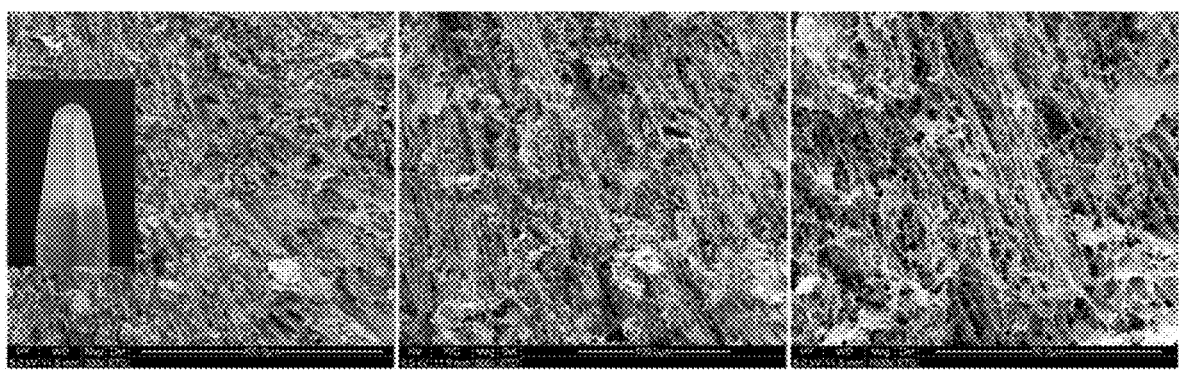
FIG. 6B is a scanning electron micrograph of collagen hydrogel and a hydrogel image for E3-VBB-K3.
Figure 6C:
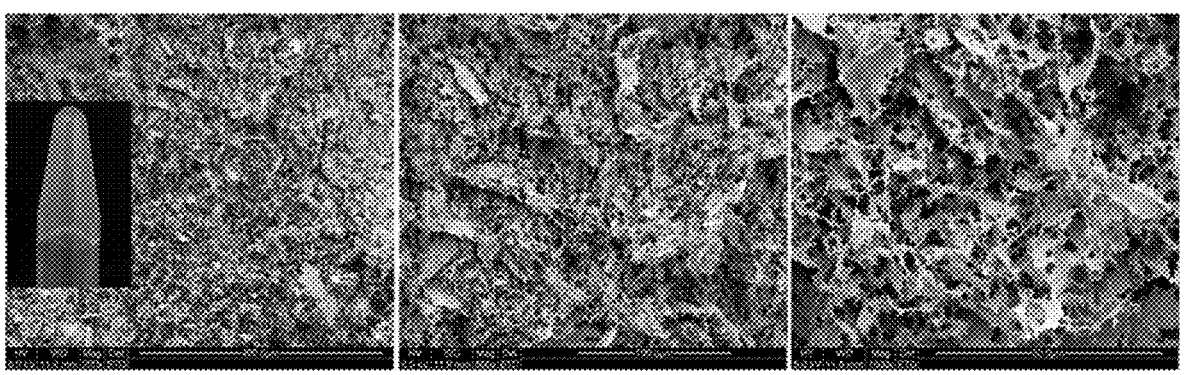
FIG. 6C is a scanning electron micrograph of collagen hydrogel and a hydrogel image for E3-VBBB-K3.

Collagen E3-VB-K3, E3-VBB-K3 and E3-VBBB-K3 purifying solutions prepared in Embodiment 1 are respectively dialyzed by 10 mM PB in a dialysis bag with a molecular weight cut-off of 7 kDa to obtain collagen hydrogel E3-VB-K3, E3-VBB-K3 and E3-VBBB-K3. As shown in FIG. 5A~5D, after a protein concentration is higher than 10 mg/mL, E3-VB-K3, E3-VBB-K3, and E3-VBBB-K3 are translucent hydrogel, and samples do not flow in an inverted transparent centrifuge tube to form the collagen hydrogel. After a small amount of hydrogel is taken and frozen by liquid nitrogen, the samples are freeze-dried in a freeze-dryer, and the internal structure of the collagen hydrogel is observed by a scanning electron microscope after gold is sprayed on cross sections. As shown in FIG. 6A~6C, the hydrogel samples of E3-VB-K3, E3-VBB-K3 and E3-VBBB-K3 all appear as loose porous collagen sponge, which can provide a good three-dimensional microenvironment for growth and differentiation of cells. The mechanical and rheological properties of hydrogel are tested. At a low concentration (<5 mg/mL), both E3-VB-K3 and E3-VBB-K3 are both liquid, and a storage modulus G' is less than a loss modulus G''; E3-VBBB-K3 reaches a gel point at a concentration of 5 mg/mL and at an angular frequency of 0.25 rad/s, and then appears as soft hydrogel when G' is greater than G''; and compared with the E3-VB-K3 and the E3-VBB-K3, by lengthening a collagen region, the solid content of the obtained hydrogel can be reduced. At a high concentration (>16 mg/mL), the E3-VB-K3, the E3-VBB-K3 and the E3-VBBB-K3 all appear as the hydrogel. For the E3-VBBB-K3, a saturation concentration thereof is 11.6 mg/mL, showing better water content, and for the E3-VB-K3, by increasing the concentration of the hydrogel, solid gel (as shown in FIG. 6A~6C) showing low water content and high mechanical strength can be prepared.

What is claimed is:

1. A method for preparing type I collagen hydrogel, comprising the following steps:
    synthesizing a gene encoding a chimeric α-helical collagen peptide chain;
    ligating the gene into an expression vector,
    transforming the expression vector into a target cell;
    incubating the target cells under condition that causes expression of the gene to produce the encoded chimeric α-helical collagen peptide chain,
    purifying the chimeric α-helical collagen peptide chain, and
    dialyzing the chimeric α-helical collagen peptide chain at 0° C. to 4_° C.,
    wherein the gene comprises a nucleotide sequence selected from any one of the SEQ ID NOs: 9 to 12.

2. The method according to claim 1, wherein the expression vector is a pColdIII plasmid or a pET plasmid.

3. The method according to claim 1, wherein the target cell is an *Escherichia coli* (*E. coli*) cell, selected from *E. coli* BL21, *E. coli* BL21(DE3), *E. coli* JM109, *E. coli* DH5α, or *E. coli* TOP10.

4. The method according to claim 1, wherein the expression vector is pColdIII; and wherein the target cell is *E. coli* BL21(DE3).

5. The method according to claim 1, wherein the chimeric α-helical collagen peptide chain dialyzed in water or a phosphate buffer solution to obtain an aggregate, and after reaching a concentration greater than or equal to 10 mg/mL, the hydrogel is formed after standing for at least 3 days at 4° C.

6. The method according to claim 1, wherein the chimeric α-helical collagen peptide chain has comprises a peptide sequence selected from any one of the SEQ ID NOs: 5 to 8.

* * * * *

SEQUENCE LISTING

```
<160> NUMBER OF SEQ ID NOS: 20

<210> SEQ ID NO 1
<211> LENGTH: 73
<212> TYPE: PRT
<213> ORGANISM: Artificial Sequence
<220> FEATURE:
<223> OTHER INFORMATION: Protein translated from synthetic DNA

<400> SEQUENCE: 1

Ala Asp Glu Gln Glu Glu Lys Ala Lys Val Arg Thr Glu Leu Ile Gln
1               5                   10                  15

Glu Leu Ala Gln Gly Leu Gly Gly Ile Glu Lys Lys Asn Phe Pro Thr
            20                  25                  30

Leu Gly Asp Glu Asp Leu Asp His Thr Tyr Met Thr Lys Leu Leu Thr
        35                  40                  45

Tyr Leu Gln Glu Arg Glu Gln Ala Glu Asn Ser Trp Arg Lys Arg Leu
    50                  55                  60

Leu Lys Gly Ile Gln Asp His Ala Leu
65                  70

<210> SEQ ID NO 2
<211> LENGTH: 7
<212> TYPE: PRT
<213> ORGANISM: Artificial Sequence
<220> FEATURE:
<223> OTHER INFORMATION: Protein translated from synthetic DNA

<400> SEQUENCE: 2

Glu Ile Ser Ala Leu Glu Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Protein translated from synthetic DNA
```

<400> SEQUENCE: 3

Lys Ile Ser Ala Leu Lys Glu
1               5

<210> SEQ ID NO 4
<211> LENGTH: 81
<212> TYPE: PRT
<213> ORGANISM: Artificial Sequence
<220> FEATURE:
<223> OTHER INFORMATION: Protein translated from synthetic DNA

<400> SEQUENCE: 4

Gly Pro Arg Gly Glu Gln Gly Pro Gln Gly Leu Pro Gly Lys Asp Gly
1               5                   10                  15
Glu Ala Gly Ala Gln Gly Pro Ala Gly Pro Met Gly Pro Ala Gly Phe
                20                  25                  30
Pro Gly Glu Arg Gly Glu Lys Gly Glu Pro Gly Thr Gln Gly Ala Lys
            35                  40                  45
Gly Asp Arg Gly Glu Thr Gly Pro Val Gly Pro Arg Gly Glu Arg Gly
        50                  55                  60
Glu Ala Gly Pro Ala Gly Lys Asp Gly Glu Arg Gly Pro Val Gly Pro
65                  70                  75                  80
Ala

<210> SEQ ID NO 5
<211> LENGTH: 157
<212> TYPE: PRT
<213> ORGANISM: Artificial Sequence
<220> FEATURE:
<223> OTHER INFORMATION: Protein translated from synthetic DNA

<400> SEQUENCE: 5

Ala Asp Glu Gln Glu Glu Lys Ala Lys Val Arg Thr Glu Leu Ile Gln
1               5                   10                  15
Glu Leu Ala Gln Gly Leu Gly Gly Ile Glu Lys Lys Asn Phe Pro Thr
                20                  25                  30
Leu Gly Asp Glu Asp Leu Asp His Thr Tyr Met Thr Lys Leu Leu Thr
            35                  40                  45
Tyr Leu Gln Glu Arg Glu Gln Ala Glu Asn Ser Trp Arg Lys Arg Leu
        50                  55                  60
Leu Lys Gly Ile Gln Asp His Ala Leu Asp Pro Gly Pro Arg Gly Glu
65                  70                  75                  80
Gln Gly Pro Gln Gly Leu Pro Gly Lys Asp Gly Glu Ala Gly Ala Gln
                85                  90                  95
Gly Pro Ala Gly Pro Met Gly Pro Ala Gly Phe Pro Gly Glu Arg Gly
            100                 105                 110
Glu Lys Gly Glu Pro Gly Thr Gln Gly Ala Lys Gly Asp Arg Gly Glu
        115                 120                 125
Thr Gly Pro Val Gly Pro Arg Gly Glu Arg Gly Glu Ala Gly Pro Ala
            130                 135                 140
Gly Lys Asp Gly Glu Arg Gly Pro Val Gly Pro Ala Gly
145                 150                 155

<210> SEQ ID NO 6
<211> LENGTH: 213
<212> TYPE: PRT
<213> ORGANISM: Artificial Sequence
<220> FEATURE:

<223> OTHER INFORMATION: Protein translated from synthetic DNA

<400> SEQUENCE: 6

```
Glu Ile Ser Ala Leu Glu Lys Glu Ile Ser Ala Leu Glu Lys Glu Ile
1               5                   10                  15
Ser Ala Leu Glu Lys Gly Gly Gly Gly Gly Gly Ala Asp Glu Gln
            20                  25                  30
Glu Glu Lys Ala Lys Val Arg Thr Glu Leu Ile Gln Glu Leu Ala Gln
                35                  40                  45
Gly Leu Gly Gly Ile Glu Lys Lys Asn Phe Pro Thr Leu Gly Asp Glu
        50                  55                  60
Asp Leu Asp His Thr Tyr Met Thr Lys Leu Leu Thr Tyr Leu Gln Glu
65                  70                  75                  80
Arg Glu Gln Ala Glu Asn Ser Trp Arg Lys Arg Leu Leu Lys Gly Ile
                85                  90                  95
Gln Asp His Ala Leu Asp Pro Gly Pro Arg Gly Glu Gln Gly Pro Gln
            100                 105                 110
Gly Leu Pro Gly Lys Asp Gly Glu Ala Gly Ala Gln Gly Pro Ala Gly
        115                 120                 125
Pro Met Gly Pro Ala Gly Phe Pro Gly Glu Arg Gly Lys Gly Glu
130                 135                 140
Pro Gly Thr Gln Gly Ala Lys Gly Asp Arg Gly Glu Thr Gly Pro Val
145                 150                 155                 160
Gly Pro Arg Gly Glu Arg Gly Glu Ala Gly Pro Ala Gly Lys Asp Gly
                165                 170                 175
Glu Arg Gly Pro Val Gly Pro Ala Gly Gly Gly Gly Gly Gly Gly
            180                 185                 190
Lys Ile Ser Ala Leu Lys Glu Lys Ile Ser Ala Leu Lys Glu Lys Ile
        195                 200                 205
Ser Ala Leu Lys Glu
    210
```

<210> SEQ ID NO 7
<211> LENGTH: 294
<212> TYPE: PRT
<213> ORGANISM: Artificial Sequence
<220> FEATURE:
<223> OTHER INFORMATION: Protein translated from synthetic DNA

<400> SEQUENCE: 7

```
Glu Ile Ser Ala Leu Glu Lys Glu Ile Ser Ala Leu Glu Lys Glu Ile
1               5                   10                  15
Ser Ala Leu Glu Lys Gly Gly Gly Gly Gly Gly Ala Asp Glu Gln
            20                  25                  30
Glu Glu Lys Ala Lys Val Arg Thr Glu Leu Ile Gln Glu Leu Ala Gln
                35                  40                  45
Gly Leu Gly Gly Ile Glu Lys Lys Asn Phe Pro Thr Leu Gly Asp Glu
        50                  55                  60
Asp Leu Asp His Thr Tyr Met Thr Lys Leu Leu Thr Tyr Leu Gln Glu
65                  70                  75                  80
Arg Glu Gln Ala Glu Asn Ser Trp Arg Lys Arg Leu Leu Lys Gly Ile
                85                  90                  95
Gln Asp His Ala Leu Asp Pro Gly Pro Arg Gly Glu Gln Gly Pro Gln
            100                 105                 110
Gly Leu Pro Gly Lys Asp Gly Glu Ala Gly Ala Gln Gly Pro Ala Gly
        115                 120                 125
```

Pro Met Gly Pro Ala Gly Phe Pro Gly Glu Arg Gly Glu Lys Gly Glu
        130                 135                 140

Pro Gly Thr Gln Gly Ala Lys Gly Asp Arg Gly Glu Thr Gly Pro Val
145                 150                 155                 160

Gly Pro Arg Gly Glu Arg Gly Glu Ala Gly Pro Ala Gly Lys Asp Gly
                165                 170                 175

Glu Arg Gly Pro Val Gly Pro Ala Gly Arg Gly Glu Gln Gly Pro
            180                 185                 190

Gln Gly Leu Pro Gly Lys Asp Gly Glu Ala Gly Ala Gln Gly Pro Ala
            195                 200                 205

Gly Pro Met Gly Pro Ala Gly Phe Pro Gly Glu Arg Gly Glu Lys Gly
        210                 215                 220

Glu Pro Gly Thr Gln Gly Ala Lys Gly Asp Arg Gly Glu Thr Gly Pro
225                 230                 235                 240

Val Gly Pro Arg Gly Glu Arg Gly Glu Ala Gly Pro Ala Gly Lys Asp
                245                 250                 255

Gly Glu Arg Gly Pro Val Gly Pro Ala Gly Gly Gly Gly Gly Gly
            260                 265                 270

Gly Lys Ile Ser Ala Leu Lys Glu Lys Ile Ser Ala Leu Lys Glu Lys
        275                 280                 285

Ile Ser Ala Leu Lys Glu
    290

<210> SEQ ID NO 8
<211> LENGTH: 375
<212> TYPE: PRT
<213> ORGANISM: Artificial Sequence
<220> FEATURE:
<223> OTHER INFORMATION: Protein translated from synthetic DNA

<400> SEQUENCE: 8

Glu Ile Ser Ala Leu Glu Lys Glu Ile Ser Ala Leu Glu Lys Glu Ile
1               5                   10                  15

Ser Ala Leu Glu Lys Gly Gly Gly Gly Gly Gly Ala Asp Glu Gln
            20                  25                  30

Glu Glu Lys Ala Lys Val Arg Thr Glu Leu Ile Gln Glu Leu Ala Gln
        35                  40                  45

Gly Leu Gly Gly Ile Glu Lys Lys Asn Phe Pro Thr Leu Gly Asp Glu
    50                  55                  60

Asp Leu Asp His Thr Tyr Met Thr Lys Leu Leu Thr Tyr Leu Gln Glu
65                  70                  75                  80

Arg Glu Gln Ala Glu Asn Ser Trp Arg Lys Arg Leu Leu Lys Gly Ile
                85                  90                  95

Gln Asp His Ala Leu Asp Pro Gly Pro Arg Gly Glu Gln Gly Pro Gln
            100                 105                 110

Gly Leu Pro Gly Lys Asp Gly Glu Ala Gly Ala Gln Gly Pro Ala Gly
        115                 120                 125

Pro Met Gly Pro Ala Gly Phe Pro Gly Glu Arg Gly Glu Lys Gly Glu
    130                 135                 140

Pro Gly Thr Gln Gly Ala Lys Gly Asp Arg Gly Glu Thr Gly Pro Val
145                 150                 155                 160

Gly Pro Arg Gly Glu Arg Gly Glu Ala Gly Pro Ala Gly Lys Asp Gly
                165                 170                 175

Glu Arg Gly Pro Val Gly Pro Ala Gly Pro Arg Gly Glu Gln Gly Pro
            180                 185                 190

Gln Gly Leu Pro Gly Lys Asp Gly Glu Ala Gly Ala Gln Gly Pro Ala
        195                 200                 205

Gly Pro Met Gly Pro Ala Gly Phe Pro Gly Glu Arg Gly Glu Lys Gly
        210                 215                 220

Glu Pro Gly Thr Gln Gly Ala Lys Gly Asp Arg Gly Glu Thr Gly Pro
225                 230                 235                 240

Val Gly Pro Arg Gly Glu Arg Gly Glu Ala Gly Pro Ala Gly Lys Asp
            245                 250                 255

Gly Glu Arg Gly Pro Val Gly Pro Ala Gly Pro Arg Gly Glu Gln Gly
        260                 265                 270

Pro Gln Gly Leu Pro Gly Lys Asp Gly Glu Ala Gly Ala Gln Gly Pro
        275                 280                 285

Ala Gly Pro Met Gly Pro Ala Gly Phe Pro Gly Glu Arg Gly Glu Lys
        290                 295                 300

Gly Glu Pro Gly Thr Gln Gly Ala Lys Gly Asp Arg Gly Glu Thr Gly
305                 310                 315                 320

Pro Val Gly Pro Arg Gly Glu Arg Gly Glu Ala Gly Pro Ala Gly Lys
            325                 330                 335

Asp Gly Glu Arg Gly Pro Val Gly Pro Ala Gly Gly Gly Gly Gly Gly
        340                 345                 350

Gly Gly Lys Ile Ser Ala Leu Lys Glu Lys Ile Ser Ala Leu Lys Glu
        355                 360                 365

Lys Ile Ser Ala Leu Lys Glu
        370                 375

<210> SEQ ID NO 9
<211> LENGTH: 509
<212> TYPE: DNA
<213> ORGANISM: Artificial Sequence
<220> FEATURE:
<223> OTHER INFORMATION: Synthetic DNA

<400> SEQUENCE: 9
ccatgggcca ccatcatcac catcatggcg ccgatgaaca ggaagagaaa gccaaagtgc    60
gcaccgaact gattcaggaa ttagcccagg gcctgggcgg catcgagaag aaaaatttcc   120
cgaccctggg cgacgaggat ctggatcata cctacatgac caaactgctg acctatctgc   180
aggagcgcga acaggccgaa aatagctggg caaacgcct gctgaaaggc attcaggatc    240
atgccttaga tcctggtcct cgtggtgagc aaggtccgca gggtctgccg gtaaggacg    300 gtgaagccgg tgcccagggt cctgcaggtc ctatgggccc ggcaggtttt ccgggtgaac   360
gcggtgaaaa aggtgaaccg ggcacccagg gcgcaaaagg cgatcgtggc gaaaccggtc   420
cggtgggtcc tcgtggtgaa cgtggtgagg ccggcccggc aggcaaagat ggtgagcgtg   480
gtccggttgg tccggccggt taaggatcc                                     509

<210> SEQ ID NO 10
<211> LENGTH: 677
<212> TYPE: DNA
<213> ORGANISM: Artificial Sequence
<220> FEATURE:
<223> OTHER INFORMATION: Synthetic DNA

<400> SEQUENCE: 10
ccatgggcca ccatcatcac catcatggcg agatcagcgc cctggagaag gaaatcagcg    60
ccctggagaa agagatcagc gccctggaaa aggtggtgg tggtggtggc ggtgccgatg    120

-continued

| | |
|---|---|
| aacaggaaga gaaagccaaa gtgcgcaccg aactgattca gggattagcc cagggcctgg | 180 |
| gcggcatcga agaaaaaat ttcccgaccc tgggcgacga ggatctggat catacctaca | 240 |
| tgaccaaact gctgacctat ctgcaggagc gcgaacaggc cgaaaatagc tggcgcaaac | 300 |
| gcctgctgaa aggcattcag gatcatgcct tagatcctgg tcctcgtggt gagcaaggtc | 360 |
| cgcagggtct gccgggtaag gacggtgaag ccggtgccca gggtcctgca ggtcctatgg | 420 |
| gcccggcagg ttttccgggt gaacgcgtg aaaaaggtga accgggcacc cagggcgcaa | 480 |
| aaggcgatcg tggcgaaacc ggtccggtgg gtcctcgtgg tgaacgtggt gaggccggcc | 540 |
| cggcaggcaa agatggtgag cgtggtccgg ttggtccggc cggtggtggt ggtggtggtg | 600 |
| gtggcaagat cagcgccctg aaggagaaaa tcagcgccct gaaagaaaaa atcagcgccc | 660 |
| tgaaagaata aggatcc | 677 |

<210> SEQ ID NO 11
<211> LENGTH: 920
<212> TYPE: DNA
<213> ORGANISM: Artificial Sequence
<220> FEATURE:
<223> OTHER INFORMATION: Synthetic DNA

<400> SEQUENCE: 11

| | |
|---|---|
| ccatgggcca tcaccaccat catcacggcg aaatcagcgc cctggaaaag gagatcagcg | 60 |
| ccctggagaa ggagattagc gcactggaaa aaggtggcgg tggtggcggt ggtgccgatg | 120 |
| aacaggaaga gaaagccaaa gtgcgcaccg aactgattca ggagctggca caaggcctgg | 180 |
| gcggcatcga gaaaaagaat ttcccgaccc tgggcgatga ggacctggat cacacctata | 240 |
| tgaccaagct gttaacctac ctgcaggaac gtgaacaggc cgagaacagc tggcgcaaac | 300 |
| gcctgctgaa aggcattcag gaccatgcct tagatccggg tccgcgtggt gagcaaggtc | 360 |
| cgcagggtct gccgggtaag gacggcgagg caggcgcaca gggtcctgca ggccctatgg | 420 |
| gtccggccgg ttttccgggt gagcgtgcg aaaaaggcga acctggcacc cagggtgcaa | 480 |
| aaggcgatcg tggtgaaaca ggccctgttg gccgcgtgg tgagcgtggt gaagcaggtc | 540 |
| ctgcaggtaa agatggcgaa cgcggtcctg tgggtccggc aggtcctcgt ggtgagcagg | 600 |
| gtccgcaagg tctgccgggt aaggatggcg aagcaggcgc acaaggtcct gccggtccga | 660 |
| tgggtccggc aggttttccg gcgaacgtg tgaaaaagg tgaaccgggc acccagggcg | 720 |
| ccaaaggtga tcgtggcgag accggtccgg ttggtcctcg tggtgaacgt ggtgaggcag | 780 |
| gcccggccgg taaagatggt gaacgtggcc cggttggtcc tgcaggtggt ggtggtggtg | 840 |
| gtggcggtaa gattagcgcc ctgaaggaga aaatcagcgc actgaaagaa aaaattagcg | 900 |
| ccctgaaaga gtaaggatcc | 920 |

<210> SEQ ID NO 12
<211> LENGTH: 1163
<212> TYPE: DNA
<213> ORGANISM: Artificial Sequence
<220> FEATURE:
<223> OTHER INFORMATION: Synthetic DNA

<400> SEQUENCE: 12

| | |
|---|---|
| ccatgggcca ccatcatcac catcatggcg agatcagcgc cctggaaaaa gaaattagcg | 60 |
| cactggagaa ggaaatcagc gccctggaga aggtggtgg tggtggcggc ggtgccgatg | 120 |
| aacaagaaga aaaggccaaa gtgcgcaccg aactgattca agaactggcc cagggcctgg | 180 |
| gtggcattga gaagaaaaat ttcccgaccc tgggcgacga agatctggat catacctata | 240 |

-continued

```
tgaccaaact gctgacatat ctgcaggagc gcgaacaagc agaaaacagc tggcgtaaac      300
gcctgctgaa aggcatccag gatcacgcat tagatcctgg cccgcgtggt gaacaaggtc      360
cgcagggtct gccgggtaaa gatggtgagg caggtgcaca gggtcctgca ggtccgatgg      420
gtccggcagg ttttcctggt gaacgtggtg aaaaaggcga accgggtaca cagggtgcca      480
agggtgatcg cggtgaaaca ggtccggttg gtcctcgtgg cgagcgtggt gaagccggtc      540
cggcaggtaa agatggcgaa cgtggccctg ttggtcctgc aggtccgcgt ggtgagcagg      600
gtcctcaggg tttaccgggc aaggatggtg aggccggtgc acaaggtccg gcaggtccta      660
tgggcccggc aggtttccct ggtgagcgtg gtgagaaggg tgaaccgggt acccaaggtg      720
caaaaggtga ccgcggcgag acaggtccgg ttggtccgcg tggtgaacgt ggtgaggccg      780
gtccggcagg caaggacggt gaacgcggtc ctgttggccc tgcaggtcct cgtggtgaac      840
agggcccgca aggcctgccg ggtaaggatg gtgaggcagg cgcacagggt ccggcaggtc      900
ctatgggtcc tgcaggtttt ccgggtgaac gcggtgagaa aggcgaacct ggtacccagg      960
gtgcaaaagg cgatcgtggc gaaaccggtc cggttggtcc gcgcggtgaa cgtggtgagg     1020
ccggtcctgc aggtaaagac ggtgaacgtg gtccggttgg cccggcaggt ggtggcggcg     1080
gcggtggcgg taagattagc gcactgaaag aaaaaatcag cgccctgaag gaaaaaatta     1140
gcgccctgaa agaataagga tcc                                              1163
```

<210> SEQ ID NO 13
<211> LENGTH: 19
<212> TYPE: DNA
<213> ORGANISM: Artificial Sequence
<220> FEATURE:
<223> OTHER INFORMATION: Synthetic DNA

<400> SEQUENCE: 13
ctcgagggat ccgaattca                                                    19

<210> SEQ ID NO 14
<211> LENGTH: 19
<212> TYPE: DNA
<213> ORGANISM: Artificial Sequence
<220> FEATURE:
<223> OTHER INFORMATION: Synthetic DNA

<400> SEQUENCE: 14
gagctccatg ggcactttg                                                    19

<210> SEQ ID NO 15
<211> LENGTH: 21
<212> TYPE: PRT
<213> ORGANISM: Artificial sequence
<220> FEATURE:
<223> OTHER INFORMATION: Protein translated from synthetic DNA

<400> SEQUENCE: 15

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 16
<211> LENGTH: 21
<212> TYPE: PRT
<213> ORGANISM: Artificial sequence
<220> FEATURE:

<223> OTHER INFORMATION: Protein translated from synthetic DNA

<400> SEQUENCE: 16

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 17
<211> LENGTH: 163
<212> TYPE: PRT
<213> ORGANISM: Artificial sequence
<220> FEATURE:
<223> OTHER INFORMATION: Protein from synthetic DNA

<400> SEQUENCE: 17

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80

Pro Gly Pro Arg Gly Glu Gln Gly Pro Gln Gly Leu Pro Gly Lys Asp
                85                  90                  95

Gly Glu Ala Gly Ala Gln Gly Pro Ala Gly Pro Met Gly Pro Ala Gly
            100                 105                 110

Phe Pro Gly Glu Arg Gly Glu Lys Gly Glu Pro Gly Thr Gln Gly Ala
        115                 120                 125

Lys Gly Asp Arg Gly Glu Thr Gly Pro Val Gly Pro Arg Gly Glu Arg
    130                 135                 140

Gly Glu Ala Gly Pro Ala Gly Lys Asp Gly Arg Gly Pro Val Gly
145                 150                 155                 160

Pro Ala Gly

<210> SEQ ID NO 18
<211> LENGTH: 220
<212> TYPE: PRT
<213> ORGANISM: Artificial sequence
<220> FEATURE:
<223> OTHER INFORMATION: Protein from synthetic DNA

<400> SEQUENCE: 18

His His His His His His Gly Glu Ile Ser Ala Leu Glu Lys Glu Ile
1               5                   10                  15

Ser Ala Leu Glu Lys Glu Ile Ser Ala Leu Lys Gly Gly Gly Gly
            20                  25                  30

Gly Gly Gly Ala Asp Glu Gln Glu Glu Lys Ala Lys Val Arg Thr Glu
            35                  40                  45

Leu Ile Gln Glu Leu Ala Gln Gly Leu Gly Gly Ile Glu Lys Lys Asn
    50                  55                  60

Phe Pro Thr Leu Gly Asp Glu Asp Leu Asp His Thr Tyr Met Thr Lys
65                  70                  75                  80

Leu Leu Thr Tyr Leu Gln Glu Arg Glu Gln Ala Glu Asn Ser Trp Arg
                85                  90                  95

Lys Arg Leu Leu Lys Gly Ile Gln Asp His Ala Leu Asp Pro Gly Pro
            100                 105                 110

Arg Gly Glu Gln Gly Pro Gln Gly Leu Pro Gly Lys Asp Gly Glu Ala
            115                 120                 125

Gly Ala Gln Gly Pro Ala Gly Pro Met Gly Pro Ala Gly Phe Pro Gly
        130                 135                 140

Glu Arg Gly Glu Lys Gly Glu Pro Gly Thr Gln Gly Ala Lys Gly Asp
145                 150                 155                 160

Arg Gly Glu Thr Gly Pro Val Gly Pro Arg Gly Glu Arg Gly Glu Ala
            165                 170                 175

Gly Pro Ala Gly Lys Asp Gly Glu Arg Gly Pro Val Gly Pro Ala Gly
            180                 185                 190

Gly Gly Gly Gly Gly Gly Lys Ile Ser Ala Leu Lys Glu Lys Ile
        195                 200                 205

Ser Ala Leu Lys Glu Lys Ile Ser Ala Leu Lys Glu
        210                 215                 220

<210> SEQ ID NO 19
<211> LENGTH: 301
<212> TYPE: PRT
<213> ORGANISM: Artificial sequence
<220> FEATURE:
<223> OTHER INFORMATION: Protein from synthetic DNA

<400> SEQUENCE: 19

His His His His His His Gly Glu Ile Ser Ala Leu Glu Lys Glu Ile
1               5                   10                  15

Ser Ala Leu Glu Lys Glu Ile Ser Ala Leu Glu Lys Gly Gly Gly Gly
            20                  25                  30

Gly Gly Gly Ala Asp Glu Gln Glu Lys Ala Lys Val Arg Thr Glu
        35                  40                  45

Leu Ile Gln Glu Leu Ala Gln Gly Leu Gly Ile Glu Lys Lys Asn
50                  55                  60

Phe Pro Thr Leu Gly Asp Glu Asp Leu Asp His Thr Tyr Met Thr Lys
65                  70                  75                  80

Leu Leu Thr Tyr Leu Gln Arg Glu Gln Ala Glu Asn Ser Trp Arg
            85                  90                  95

Lys Arg Leu Leu Lys Gly Ile Gln Asp His Ala Leu Asp Pro Gly Pro
            100                 105                 110

Arg Gly Glu Gln Gly Pro Gln Gly Leu Pro Gly Lys Asp Gly Glu Ala
            115                 120                 125

Gly Ala Gln Gly Pro Ala Gly Pro Met Gly Pro Ala Gly Phe Pro Gly
        130                 135                 140

Glu Arg Gly Glu Lys Gly Glu Pro Gly Thr Gln Gly Ala Lys Gly Asp
145                 150                 155                 160

Arg Gly Glu Thr Gly Pro Val Gly Pro Arg Gly Glu Arg Gly Glu Ala
            165                 170                 175

Gly Pro Ala Gly Lys Asp Gly Glu Arg Gly Pro Val Gly Pro Ala Gly
            180                 185                 190

Pro Arg Gly Glu Gln Gly Pro Gln Gly Leu Pro Gly Lys Asp Gly Glu
            195                 200                 205

Ala Gly Ala Gln Gly Pro Ala Gly Pro Met Gly Pro Ala Gly Phe Pro
        210                 215                 220

Gly Glu Arg Gly Glu Lys Gly Glu Pro Gly Thr Gln Gly Ala Lys Gly
225                 230                 235                 240

```
Asp Arg Gly Glu Thr Gly Pro Val Gly Pro Arg Gly Glu Arg Gly Glu
                245                 250                 255

Ala Gly Pro Ala Gly Lys Asp Gly Glu Arg Gly Pro Val Gly Pro Ala
            260                 265                 270

Gly Gly Gly Gly Gly Gly Gly Lys Ile Ser Ala Leu Lys Glu Lys
        275                 280                 285

Ile Ser Ala Leu Lys Glu Lys Ile Ser Ala Leu Lys Glu
    290                 295                 300

<210> SEQ ID NO 20
<211> LENGTH: 382
<212> TYPE: PRT
<213> ORGANISM: Artificial sequence
<220> FEATURE:
<223> OTHER INFORMATION: Protein from synthetic DNA

<400> SEQUENCE: 20

His His His His His His Gly Glu Ile Ser Ala Leu Glu Lys Glu Ile
1               5                   10                  15

Ser Ala Leu Glu Lys Glu Ile Ser Ala Leu Glu Lys Gly Gly Gly Gly
            20                  25                  30

Gly Gly Gly Ala Asp Glu Gln Glu Lys Ala Lys Val Arg Thr Glu
        35                  40                  45

Leu Ile Gln Glu Leu Ala Gln Gly Leu Gly Gly Ile Glu Lys Lys Asn
50                  55                  60

Phe Pro Thr Leu Gly Asp Glu Asp Leu Asp His Thr Tyr Met Thr Lys
65                  70                  75                  80

Leu Leu Thr Tyr Leu Gln Glu Arg Glu Gln Ala Glu Asn Ser Trp Arg
                85                  90                  95

Lys Arg Leu Leu Lys Gly Ile Gln Asp His Ala Leu Asp Pro Gly Pro
            100                 105                 110

Arg Gly Glu Gln Gly Pro Gln Gly Leu Pro Gly Lys Asp Gly Glu Ala
        115                 120                 125

Gly Ala Gln Gly Pro Ala Gly Pro Met Gly Pro Ala Gly Phe Pro Gly
    130                 135                 140

Glu Arg Gly Glu Lys Gly Glu Pro Gly Thr Gln Gly Ala Lys Gly Asp
145                 150                 155                 160

Arg Gly Glu Thr Gly Pro Val Gly Pro Arg Gly Glu Arg Gly Glu Ala
                165                 170                 175

Gly Pro Ala Gly Lys Asp Gly Glu Arg Gly Pro Val Gly Pro Ala Gly
            180                 185                 190

Pro Arg Gly Glu Gln Gly Pro Gln Gly Leu Pro Gly Lys Asp Gly Glu
        195                 200                 205

Ala Gly Ala Gln Gly Pro Ala Gly Pro Met Gly Pro Ala Gly Phe Pro
    210                 215                 220

Gly Glu Arg Gly Glu Lys Gly Glu Pro Gly Thr Gln Gly Ala Lys Gly
225                 230                 235                 240

Asp Arg Gly Glu Thr Gly Pro Val Gly Pro Arg Gly Glu Arg Gly Glu
                245                 250                 255

Ala Gly Pro Ala Gly Lys Asp Gly Glu Arg Gly Pro Val Gly Pro Ala
            260                 265                 270

Gly Pro Arg Gly Glu Gln Gly Pro Gln Gly Leu Pro Gly Lys Asp Gly
        275                 280                 285

Glu Ala Gly Ala Gln Gly Pro Ala Gly Pro Met Gly Pro Ala Gly Phe
    290                 295                 300
```

```
Pro Gly Glu Arg Gly Glu Lys Gly Glu Pro Gly Thr Gln Gly Ala Lys
305                 310                 315                 320

Gly Asp Arg Gly Glu Thr Gly Pro Val Gly Pro Arg Gly Glu Arg Gly
                325                 330                 335

Glu Ala Gly Pro Ala Gly Lys Asp Gly Glu Arg Gly Pro Val Gly Pro
            340                 345                 350

Ala Gly Gly Gly Gly Gly Gly Gly Lys Ile Ser Ala Leu Lys Glu
        355                 360                 365

Lys Ile Ser Ala Leu Lys Glu Lys Ile Ser Ala Leu Lys Glu
        370                 375                 380
```